(12) United States Patent  (10) Patent No.: US 8,845,591 B2
Ishizaki et al.  (45) Date of Patent: Sep. 30, 2014

(54) SELF-ADMINISTRATION DEVICE FOR LIQUID MEDICINE

(75) Inventors: Akihiko Ishizaki, Osaka (JP);
Katsuhiro Hiejima, Osaka (JP);
Tomohiro Uchimura, Osaka (JP)

(73) Assignee: Nipro Corporation, Osaka-shi (JP)

( * ) Notice: Subject to any disclaimer, the term of this patent is extended or adjusted under 35 U.S.C. 154(b) by 173 days.

(21) Appl. No.: 12/659,615

(22) Filed: Mar. 15, 2010

(65) Prior Publication Data

US 2010/0249718 A1   Sep. 30, 2010

(30) Foreign Application Priority Data

Mar. 25, 2009  (JP) ................. 2009-075043

(51) Int. Cl.
*A61M 5/178* (2006.01)
*A61M 37/00* (2006.01)
*A61M 5/00* (2006.01)
*A61M 5/142* (2006.01)

(52) U.S. Cl.
CPC ......... *A61M 5/1424* (2013.01); *A61M 5/14212* (2013.01)
USPC ............................ 604/185; 604/131; 604/247

(58) Field of Classification Search
USPC ......... 604/131, 181, 132, 185–189, 232, 139, 604/141–156, 246–249, 167.01–167.02, 48, 604/19, 93.01, 157, 197, 201, 110
See application file for complete search history.

(56) References Cited

U.S. PATENT DOCUMENTS

| 5,080,648 | A | 1/1992 | D'Antonio |
| 5,318,522 | A | 6/1994 | D'Antonio |
| 5,569,190 | A | 10/1996 | D'Antonio |
| 5,891,102 | A * | 4/1999 | Hiejima et al. ............... 604/185 |
| 5,931,814 | A * | 8/1999 | Alex et al. ..................... 604/131 |
| 6,027,491 | A * | 2/2000 | Hiejima et al. ............ 604/891.1 |
| 6,056,716 | A | 5/2000 | D'Antonio et al. |
| 6,213,981 | B1 * | 4/2001 | Hiejima et al. ............... 604/185 |
| 6,270,481 | B1 * | 8/2001 | Mason et al. ................. 604/181 |

(Continued)

FOREIGN PATENT DOCUMENTS

EP  0 465 267 A1  1/1992
EP  0 941 741 A2  9/1999

(Continued)

OTHER PUBLICATIONS

Extended European Search Report issued in corresponding European Application No. EP 10 00 2824.0 dated Apr. 19, 2011.

(Continued)

*Primary Examiner* — Kevin C Sirmons
*Assistant Examiner* — William Carpenter
(74) *Attorney, Agent, or Firm* — Oliff PLC

(57) ABSTRACT

A liquid medicine self-administration device including a flexible reservoir, an operating member, a pushing member to move with respect to the operating member and to induce pressure deformation of the reservoir, and engaging means engages the operating member. With the operating member engaged by the engaging means, the pushing member is relatively moved to the operating member based on restoring force of a spring member to push the reservoir by the pushing member. By disengaging means moving in unison with the pushing member, the engaging means is released from an engaged state with respect to the operating member, when the pushing member has moved to a predetermined location while pushing the reservoir.

7 Claims, 13 Drawing Sheets

(56) References Cited

U.S. PATENT DOCUMENTS

| | | | |
|---|---|---|---|
| 6,979,316 B1 * | 12/2005 | Rubin et al. | 604/156 |
| 2004/0127860 A1 * | 7/2004 | Rake et al. | 604/246 |
| 2007/0191780 A1 * | 8/2007 | Modi | 604/187 |

FOREIGN PATENT DOCUMENTS

| | | |
|---|---|---|
| JP | A-2-500340 | 2/1990 |
| JP | A-4-109957 | 4/1992 |
| JP | A-2007-111179 | 5/2007 |
| WO | WO 88/09677 A1 | 12/1988 |

OTHER PUBLICATIONS

Japanese Office Action dated Jan. 29, 2013 for Japanese Patent Application No. 2009-075043 (with partial translation).

Jun. 7, 2012 Office Action issued in Chinese Patent Application No. 201010148937.5 (with translation).

Chinese Office Action dated Feb. 18, 2013 in Chinese Application No. 201010148937.5 (with translation).

Sep. 24, 2013 Office Action issued in Japanese Patent Application No. 2009-075043 (with partial translation).

* cited by examiner

SELF-ADMINISTRATION DEVICE FOR LIQUID MEDICINE

INCORPORATED BY REFERENCE

The disclosure of Japanese Patent Application No. 2009-075043 filed on Mar. 25, 2009 including the specification, drawings and abstract is incorporated herein by reference in its entirety.

BACKGROUND OF THE INVENTION

1. Field of the Invention

The present invention relates in general to a self-administration device for liquid medicines, and in particular to an improvement to a liquid medicine self-administration device that enables a patient to self-administer a liquid medicine such as an analgesic or anesthetic.

2. Description of the Related Art

In the field of anesthesiology, administration of liquid medicines by an epidural catheter insertion method employing a low-dose continuous injection instrument has come into use in recent years as a way to alleviate pain such as postoperative or cancerous pain. However, due to variability in medical condition or constitution among patients, there will be instances in which a patient may report sudden severe pain despite being continuously administered a low dose of an analgesic. Accordingly, currently in development are liquid medicine self-administration devices which allow a patient to self-administer a large dose of an analgesic in a single shot in order to rapidly treat such occasional symptoms.

Given this background, the Applicant previously proposed a liquid medicine self-administration device having a number of outstanding features (see U.S. Pat. No. 6,213,981). This liquid medicine self-administration device includes a cylindrical housing (casing) wherein a base member (port portion) having a liquid medicine inlet/outlet port and capable of flexural deformation is attached fitting into one open end of the housing, and pushing means is inserted into the other open end so as to be slidable in the axial direction. Within the housing there is accommodated a reservoir of pouch form that, when arranged with an opening thereof communicating with the liquid medicine inlet/outlet port of the base member, is closed by the base member and retains liquid medicine that has been injected through the liquid medicine inlet/outlet port. By then sliding the pushing means, through flexural deformation of the reservoir induced by being pushed by the pushing means, the liquid medicine retained within the reservoir will be expelled through the inlet/outlet port. Using this liquid medicine self-administration device, the patient can push and slide the pushing means in order to self-administer a one-time large dose of a liquid medicine containing an analgesic or the like.

With such a liquid medicine self-administration device, the pushing means in particular is composed of a cylindrical operating member (operating member) that has been slidably inserted into a first open end of the housing, and a spring member housed inside the operating member and adapted to undergo elastic deformation when the operating member is slid towards the base member end. Engaging means is also provided for engaging (locking) the operating member when the operating member has reached a slide end position situated at the base member end, so that the operating member is non-slidably locked. With the operating member in the locked state, the reservoir will undergo pressure deformation due to the restoring force of the elastically deformed spring member.

Using such a liquid medicine self-administration device, the patient need merely push the operating member until it is locked by the engaging means; subsequently, through the restoring force of the spring member, the liquid medicine that was retained in the reservoir will be administered to the patient automatically under constant pressure. For this reason, in contrast to the case where a conventional liquid medicine self-administration device lacking such engaging means is used, it is unnecessary for the patient to continue to push the pushing means until the entire amount of liquid medicine inside the reservoir has been completely expelled, and it is also possible to avoid abrupt expulsion of liquid medicine from the reservoir due to the pushing means having been pushed with excessive force. Consequently, through the use of the proposed liquid medicine self-administration device, even a patient with diminished physical strength will be able to self-administer liquid medicine in a stable and reliable manner, and it will be possible to effectively prevent liquid medicine from leaking due to being expelled too abruptly.

The liquid medicine self-administration device has been designed so that, through a manual operation performed after the liquid medicine in the reservoir has been expelled to release the operating member from the locked state of engagement by the engaging means, the reservoir will recover to its condition prior to deformation through the pressure of injection of liquid medicine into the reservoir. In association with the recover of the reservoir, the operating member will return from the slide end position to its position prior to being pushed. Thus, in the event that the patient has forgotten to perform the unlocking operation, it will be necessary to perform unlocking and to then wait until the reservoir has refilled with liquid medicine before the next shot of liquid medicine can be administered.

SUMMARY OF THE INVENTION

It is therefore one object of this invention to provide a liquid medicine self-administration device of improved construction whereby once the liquid medicine in the reservoir has been expelled, the operating member will be released automatically from its state of engagement with the engaging means, so that the reservoir may be refilled with liquid medicine, without the need to perform any kind of manual operation.

One aspect of the present invention provides a liquid medicine self-administration device comprising: a housing open at both ends; a base member having a liquid medicine inlet/outlet port and attached fitting into a first open end of the housing; a flexible reservoir having an open end and a closed end wherein the open end is closed by the base member, arranged accommodated within the housing with the interior in communication with the liquid medicine inlet/outlet port of the base member and adapted to retain liquid medicine that has been injected therein through the liquid medicine inlet/outlet port; an operating member inserted through another open end of the housing and adapted to undergo movement into proximity with and away from the reservoir through an operation performed from an outside; engaging means adapted to engage the operating member when the operating member has moved into proximity with the reservoir and to prevent movement of the operating member; a pushing member accommodated in the housing interior between the operating member and the reservoir so as to be capable of relative movement with respect to the operating member, and adapted, through relative movement with respect to the operating member, to push against and induce flexural deformation of the reservoir causing liquid medicine inside the reservoir to be expelled from the liquid medicine inlet/outlet port; a spring member arranged within the housing in such a way as to undergo elastic deformation between the operating member and the pushing member through movement of the operating member into proximity with the reservoir, and to exhibit restoring force from an elastically deformed state in which the operating member has been engaged by the engaging means so that the relative movement of the pushing member with respect to the operating member resulting from the restoring force causes the reservoir to be pushed by the pushing member; and disengaging means arranged inside the housing so as to be capable of movement in unison with the pushing member and, when the pushing member has moved to a predetermined location while pushing the reservoir, functioning to release the engaging means from an engaged state with respect to the operating member.

In one preferred form of the present invention, the disengaging means is composed of a disengaging projection integrally projecting towards the base member end from the pushing member; the engaging means includes an engaging portion disposed on the operating member, a flexing member capable of flexural deformation non-displaceably disposed between the reservoir and the pushing member, an engaging claw portion projecting from the flexing member and adapted to engage the engaging portion of the operating member, and a sloping face adapted to be pushed by the disengaging projection when the pushing member has moved towards the reservoir end and to bring about flexural deformation of the flexing member; and the engaging claw portion is released from the engaged state with respect to the engaging portion of the operating member through flexural deformation of the flexing member in association with pushing of the sloping face by the disengaging projection.

Where the design of the engaging means includes the flexing member as described above, preferably, the flexing member is composed of a split ring; and the engaging claw portion is released from the engaged state with respect to the engaging portion of the operating member through flexion and diameter constriction of the split ring brought about by the disengaging projection of the pushing member pushing against the sloping face.

In another preferred form of the invention, the engaging means is situated housed inside the housing having a window; and the flexing member is furnished with an operating projection that projects to the housing exterior through the window so that, with the engaging claw portion in the engaged state with respect to the engaging portion of the operating member, the flexing member undergoes flexural deformation when the operating projection is pushed from the outside, in order to release the engaging claw portion from the engaged state with respect to the engaging portion of the operating member.

Another aspect of the present invention provides a liquid medicine self-administration device including a flexible reservoir having a liquid medicine inlet and a liquid medicine outlet and adapted to retain a prescribed amount of liquid medicine in an interior thereof, and pushing means adapted to induce pressure deformation of the reservoir and expel liquid medicine inside the reservoir from the liquid medicine outlet, wherein the improvement comprises: the pushing means having an operating member adapted to undergo movement into proximity with and away from the reservoir through an operation performed from an outside, and a pushing member adapted to undergo relative movement with respect to the operating member and to induce pressure deformation of the reservoir; engaging means adapted to engage the operating member when the operating member has moved into proximity with the reservoir and to prevent movement of the operating member; a spring member adapted to undergo elastic deformation through movement of the operating member towards the reservoir, and with the operating member engaged by the engaging means, to produce relative movement of the pushing member with respect to the operating member on the basis of restoring force from the elastically deformed state so that the reservoir is pushed by the pushing member; and disengaging means adapted to move in unison with the pushing member and, when the pushing member has moved to a predetermined location while pushing the reservoir, to release the engaging means from the engaged state with respect to the operating member.

With the liquid medicine self-administration device according to the present invention, simply by pushing the operating member so that it is engaged by the engaging means and becomes locked thereby, the reservoir will undergo flexural deformation while pushed by the pushing member due to the restoring force of the spring member, thus causing liquid medicine retained inside the reservoir to be expelled automatically at constant pressure. Then, once the pushing member has moved to a prescribed position while pushing on the reservoir, the operating member will be disengaged from the engaging means by the disengaging means so that the operating member again assumes a slidable state. The spring member is thereby released from a state of elastic deformation, whereupon the spring member recovers and pushing of the reservoir by the pushing member due to the restoring force of the spring member ceases. In this state, owing to injection pressure of liquid medicine into the reservoir through the liquid medicine inlet, the reservoir will recover from a state of flexural deformation, and liquid medicine will again fill the reservoir interior.

According to the liquid medicine self-administration device of the present invention, by only setting the movement zone of the pushing member when engagement of the operating member by the engaging means is released by the engaging means to the movement zone of the pushing member when expulsion of liquid medicine inside the reservoir is complete, engagement of the operating member by the engaging means, i.e., locking of the operating member, can be released automatically at the point in time that liquid medicine inside the reservoir is finished being expelled. This makes it possible for the reservoir interior to refill with liquid medicine without the need to perform any manual operation. As a result, it is possible to effectively eliminate situations where administration of a subsequent shot of liquid medicine cannot take place due to having neglected to unlock the operating member, thus affording further enhanced ease of use in a very advantageous manner.

BRIEF DESCRIPTION OF THE DRAWINGS

The foregoing and/or other objects features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
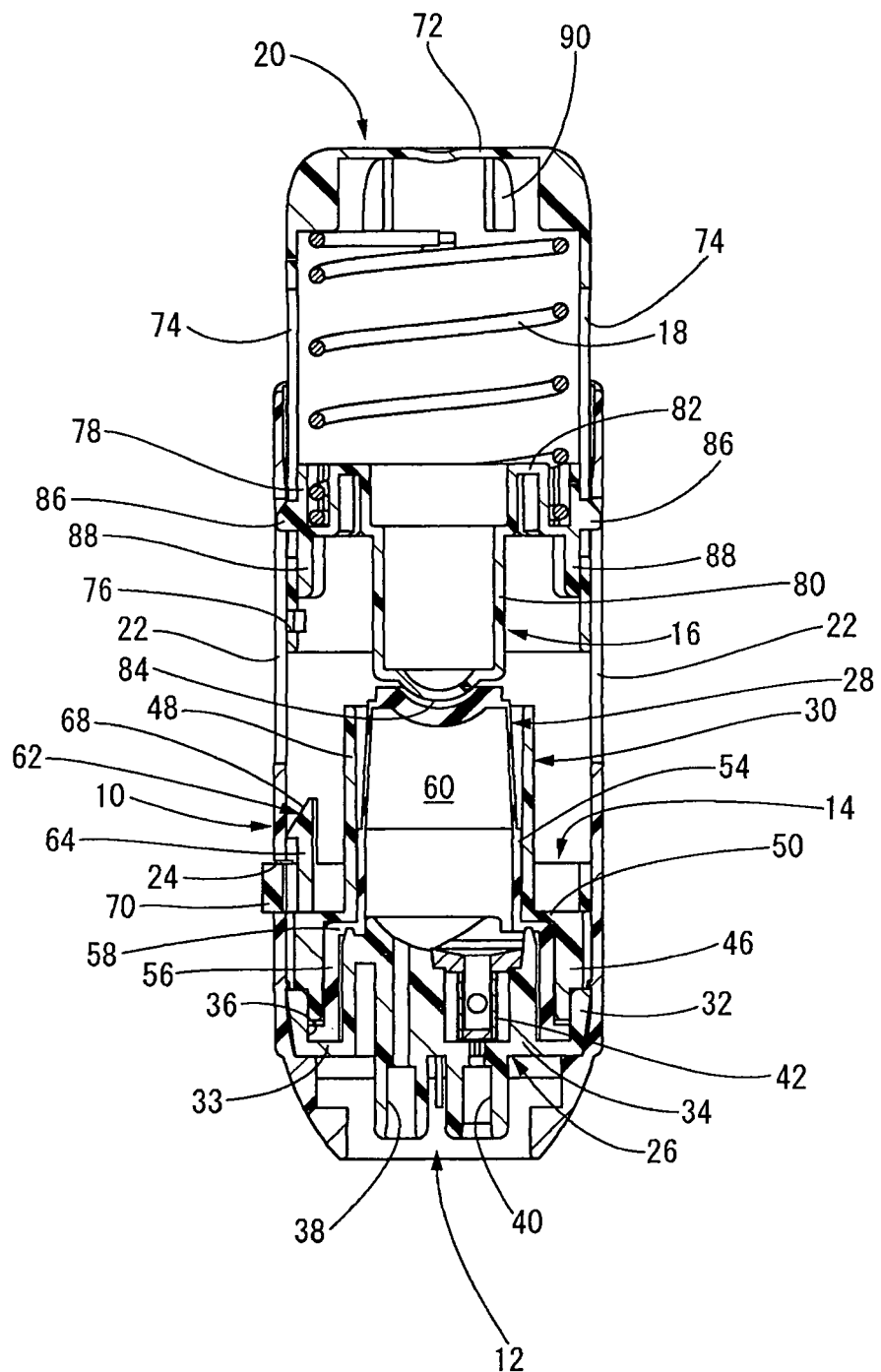
FIG. 1 is a longitudinal sectional view depicting one embodiment of a liquid medicine self-administration device according to the present invention.
Figure 2:
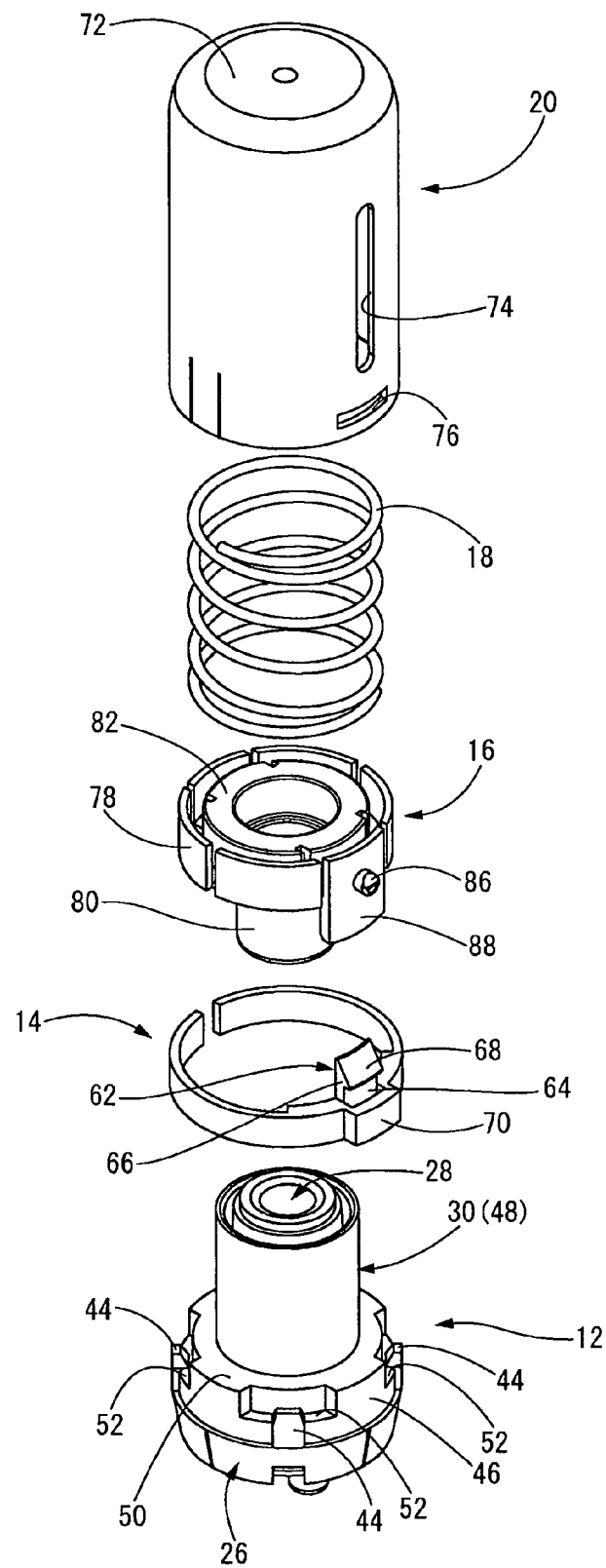
FIG. 2 is an exploded perspective view of the liquid medicine self-administration device of FIG. 1, shown with the housing removed.

First, FIG. 1 depicts a longitudinal sectional view of one embodiment of a liquid medicine self-administration device according to the present invention; and FIG. 2 depicts an exploded perspective view thereof. It will be appreciated from the drawings that the liquid medicine self-administration device of the present embodiment has a housing 10, a reservoir unit 12, a split ring 14 provided as a flexing member, a plunger 16 provided as a pushing member, a helical compression spring 18 provided as a spring member; and a push button 20 provided as an operating member. In FIG. 2, the housing 10 is shown removed.

Turning to a more detailed description, the housing 10 is a cylindrical member of approximately round cylindrical shape extending in the vertical direction in FIG. 1, and made using synthetic resin material, for example, polyethylene, polypropylene, polyester, polyvinyl chloride, polycarbonate, or polyacetal. For convenience, hereinbelow the direction corresponding to the vertical direction of FIG. 1 in the liquid medicine self-administration device of the present embodiment shall be referred to as the vertical direction.

In this cylindrical housing 10, the lower end portion has tapered cylindrical shape progressively smaller in diameter towards the bottom so that the opening at the lower end is smaller in diameter than the opening at the upper end. In zones situated in diametrical opposition in the axially medial portion of the housing 10 there are formed slits 22 that extend for mutually identical length in the axial direction, with one being formed in each of the zones. A window 24 of oblong shape is formed to the lower side of one of the slits 22 in the housing 10 and passes completely through the lower end of the housing 10.

Figure 3:
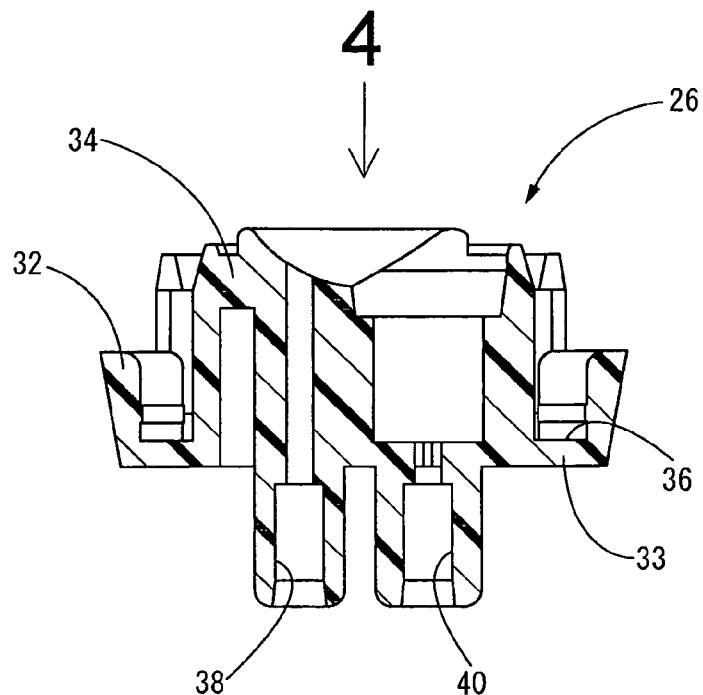
FIG. 3 is a longitudinal sectional view of a base member which is part of the liquid medicine self-administration device of FIG. 1, taken along line 3-3 in FIG. 4.
Figure 4:
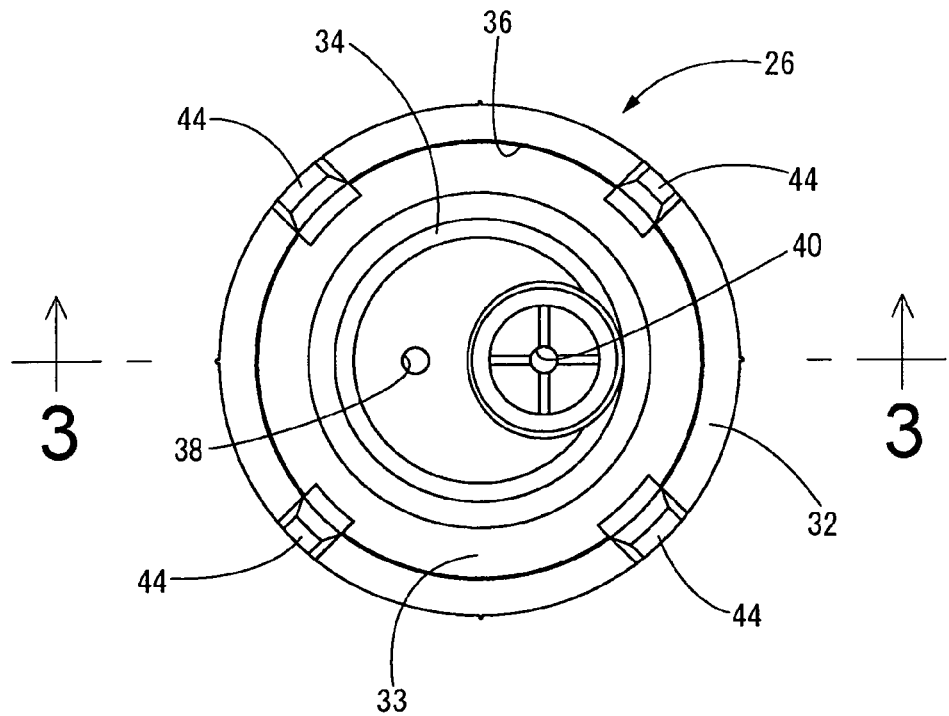
FIG. 4 is an illustration viewed in the direction of arrow 4 in FIG. 3.

The reservoir unit 12 fits inside the lower end part of the housing 10. The reservoir unit 12 is composed of a base member 26, a reservoir 28, and a reservoir ring 30. The base member 26 is a molded resin component made using resin material comparable to the material forming the housing 10. As shown in FIGS. 2 to 4, the base member 26 integrally incorporates a mounting ring portion 32, and a port portion 34 having a round cylindrical outside peripheral face positioned concentrically to the inside of this mounting ring portion 32 and linked to the mounting ring portion 32 by a linking portion 33 of annular disk shape. Between the mounting ring portion 32 and the port portion 34 there is defined a groove portion 36 of approximately annular form whose respective side walls are defined by the inside peripheral face and outside peripheral face of these portions and whose basal portion is defined by the linking portion 33 so that the mounting ring portion 32 is elastically deformable diametrically inward.

The port portion 34 of the base member 26 is provided with a liquid medicine inlet port 38 provided as a liquid medicine inlet, and a liquid medicine outlet port 40 provided as a liquid medicine outlet, these being disposed so as to pass completely through the port portion 34 in the vertical direction. The liquid medicine inlet port 38 and the liquid medicine outlet port 40 are also designed as liquid medicine inlet/outlet ports. As depicted in FIG. 1, a constant pressure-opening valve 42 is fitted into the interior of the liquid medicine outlet port 40. This constant pressure-opening valve 42 has a known art design adapted to open when pressure inside the liquid medicine outlet port 40 has reached a predetermined value. Here, in order to make possible continuous administration of a low dose of liquid medicine to the patient as described later, the constant pressure-opening valve 42 has been designed to open in response to a rise in pressure inside the liquid medicine outlet port 40 occurring when a small amount of liquid medicine is injected into the reservoir 28 through the liquid medicine inlet port 38. On the upper end face of the mounting ring portion 32, a hook portion 44 furnished at its distal end with a barb-shaped claw has been integrally formed projecting upright at each of four locations spaced equidistantly in the circumferential direction.

Figure 5:
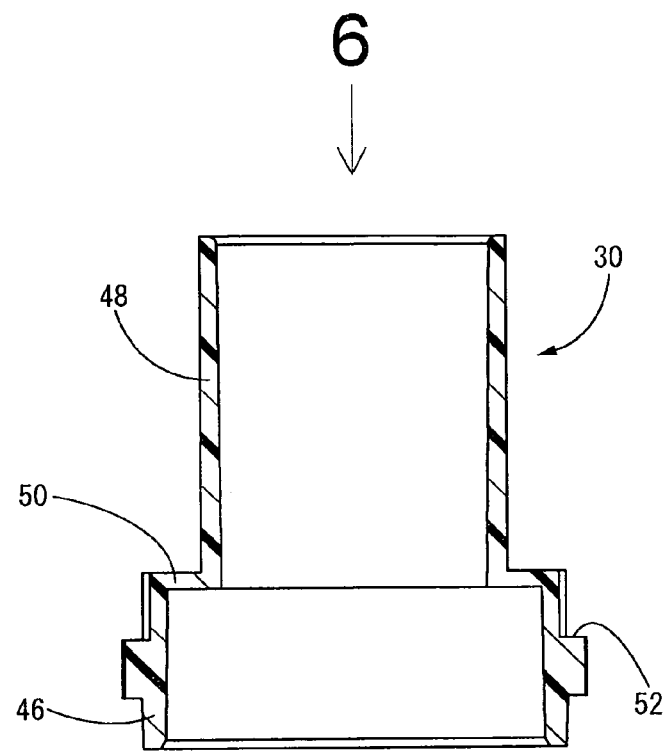
FIG. 5 is a longitudinal sectional view of a reservoir ring which is part of the liquid medicine self-administration device of FIG. 1, taken along line 5-5 in FIG. 6.
Figure 6:
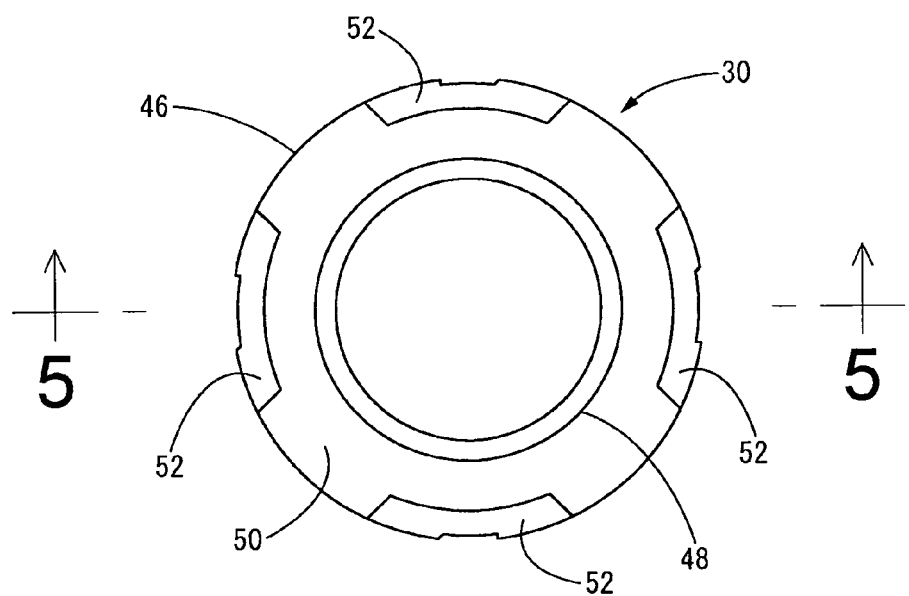
FIG. 6 is an illustration viewed in the direction of arrow 6 in FIG. 5.

The reservoir ring 30 is likewise a molded resin component made using resin material comparable to the material forming the housing 10 and the base member 26. As shown in FIGS. 5 and 6, the reservoir ring 30 as a whole has an approximately round stepped cylindrical shape wherein the lower end section defines a large-diameter portion 46, the upper end section defines a small-diameter portion 48, and the axially medial portion defines a step portion 50 of shoulder form providing a stepped transition between the large-diameter portion 46 and the small-diameter portion 48. An engagement recess 52 is formed at each of four locations spaced equidistantly in the circumferential direction of the step portion 50.

Figure 7:
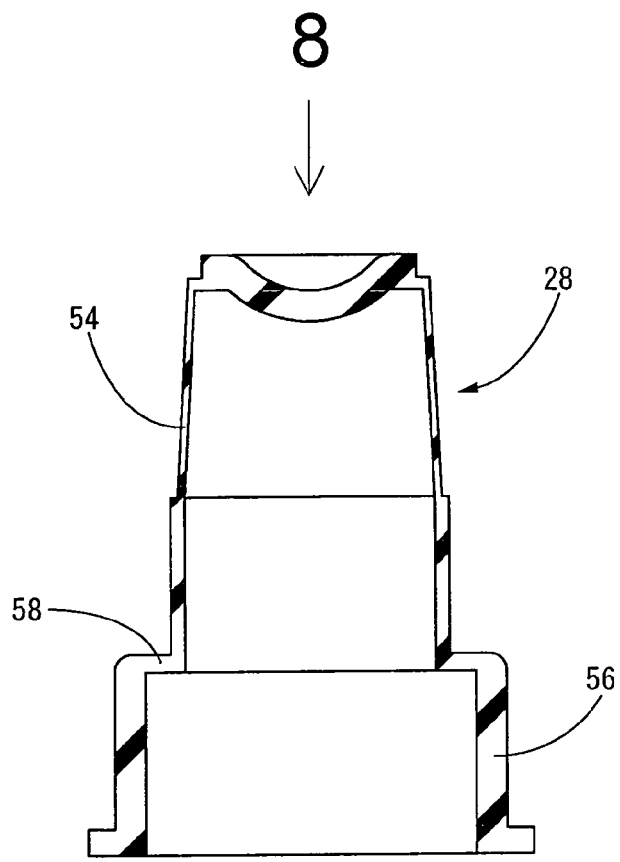
FIG. 7 is a longitudinal sectional view of a reservoir which is part of the liquid medicine self-administration device of FIG. 1, taken along line 7-7 in FIG. 8.
Figure 8:
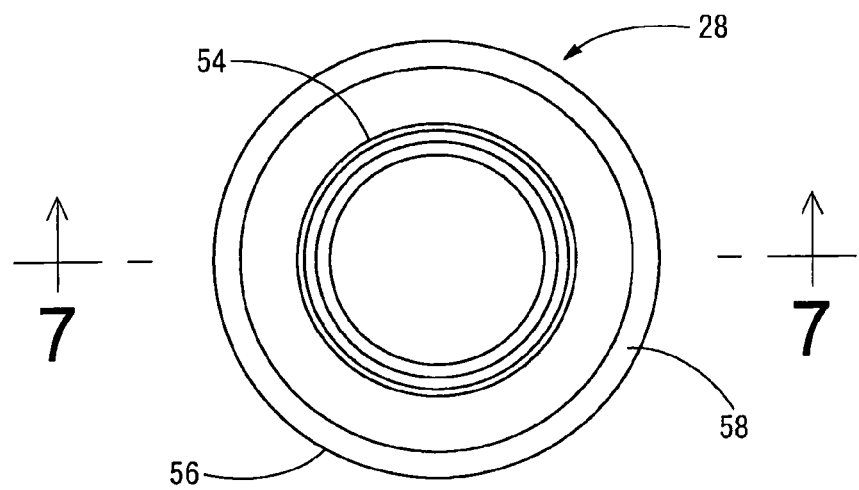
FIG. 8 is an illustration viewed in the direction of arrow 8 in FIG. 7.

Meanwhile, the reservoir 28 is made using elastic materials such as elastomers, silicone rubber or other such synthetic rubbers, or natural rubber. As shown in FIGS. 7 and 8, the shape of the reservoir 28 as a whole is a bottomed, approximately round stepped cylindrical shape having an upper base panel and slightly smaller than the reservoir ring 30. The upper section of the reservoir 28 defines a small-diameter portion 54 which is thin and readily elastically deformable, while the lower section defines a thick-walled large-diameter portion 56, with a step portion 58 of shoulder form formed in the axially medial portion providing a stepped transition between the small-diameter portion 54 and the large-diameter portion 56.

As depicted in FIGS. 1 and 2, the reservoir 28 is arranged with the bottom end part of its large-diameter portion 56 intruding into the groove portion 36 of the base member 26 and with its large-diameter portion 56 fitting externally about the port portion 34, with the bottom face of the step portion 58 positioned in contact about the entire circumference against the outside peripheral part of the upper end face of the port portion 34. The reservoir ring 30, which is elongated in an axial direction with respect to the housing 10 such that it extends substantially the length of the reservoir 28, is slipped externally about the reservoir 28 so that their respective small-diameter portions 54, 48 correspond and their large-diameter portions 56, 46 correspond, with the step portion 50 of the reservoir ring 30 juxtaposed over the step portion 58 of the reservoir 28, and the lower end part of the large-diameter portion 46 slipped into the groove portion 36 of the base member 26. In this state, the four hook portions 44, 44, 44, 44 which integrally rise up from the mounting ring portion 32 of the base member 26 will respectively engage the four engagement recesses 52, 52, 52, 52 which have been provided to the step portion 50 of the reservoir ring 30.

By so doing the reservoir ring 30 is integrally attached to the base member 26 with the reservoir 28 held clasped between the base member 26 and the reservoir ring 30. In this clasped state, the opening leading from the small-diameter portion 54 to the large-diameter portion 56 of the reservoir 28 will be closed off by the port portion 34 of the base member 26 so that the interior space of the small-diameter portion 54 defines a liquid medicine retaining portion 60 sealed off liquidtightly from the outside. This liquid medicine retaining portion 60 communicates with the outside only through the liquid medicine inlet port 38 and the liquid medicine outlet port 40. The small-diameter portion 54 of the reservoir 28 which defines this liquid medicine retaining portion 60 is housed inside the small-diameter portion 48 of the reservoir ring 30 so that the small-diameter portion 48 protects the small-diameter portion 54 of the reservoir 28.

In this way, in the present embodiment, the reservoir unit 12 is constituted as an integral assembly of the base member 26, the reservoir 28, and the reservoir ring 30. The reservoir unit 12 is then slipped into the housing 10 from its upper opening, and the mounting ring portion 32 of the base member 26, placed in a state of elastic deformation diametrically inward, is disposed in pressure contact with the inside peripheral face of the lower end part of the housing 10 to secure it to the inside of the lower end part of the housing 10. The base member 26 is thereby installed inside the lower opening of the housing 10, with the reservoir 28 accommodated inside the lower end part of the housing 10. The liquid medicine inlet port 38 and the liquid medicine outlet port 40 which have been provided to the port portion 34 of the base member 26 open to the outside through the lower opening of the housing 10, and the liquid medicine retaining portion 60 of the reservoir 28 communicates with the outside through these two ports 38, 40.

The reservoir 28 employed in this instance is one with a small-diameter portion 54 capacity of about 3 mL, allowing about 3 mL of liquid medicine to be retained inside the liquid medicine retaining portion 60. If the amount of liquid medicine to be retained within the liquid medicine retaining portion 60 of the reservoir 28 will be less than this, while not depicted in the drawings, for example, a reservoir having a small-diameter portion having the same diameter but lower height giving it smaller capacity could be incorporated into the reservoir unit assembly. On the other hand, if it is desired to increase the retained amount of liquid medicine within the liquid medicine retaining portion 60, for example, a reservoir having a small-diameter portion having the same diameter but greater height giving it larger capacity could be incorporated into the reservoir unit assembly. In the present embodiment, the reservoir 28 is incorporated into the reservoir unit 12 assembly as described above, thereby allowing the reservoir 28 to be easily replaced, and allowing the capacity of the liquid medicine retaining portion 60 to be easily increased or decreased as well.

Figure 9:
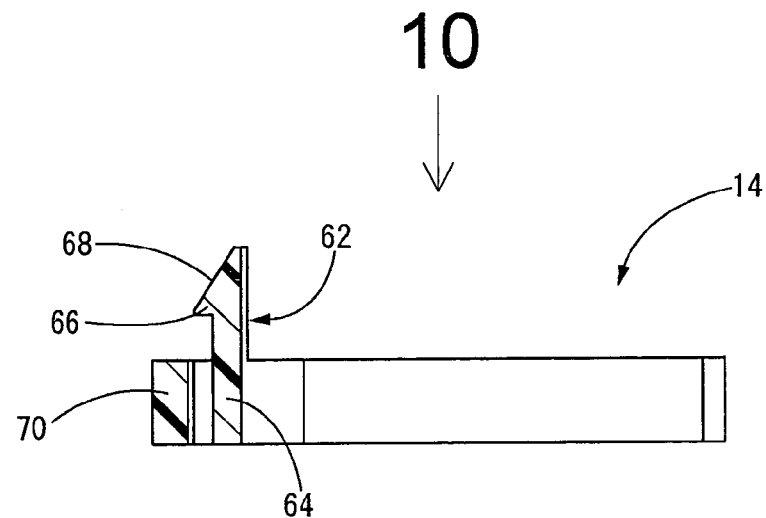
FIG. 9 is a longitudinal sectional view of a split ring which is part of the liquid medicine self-administration device of FIG. 1, taken along line 9-9 in FIG. 10.
Figure 10:
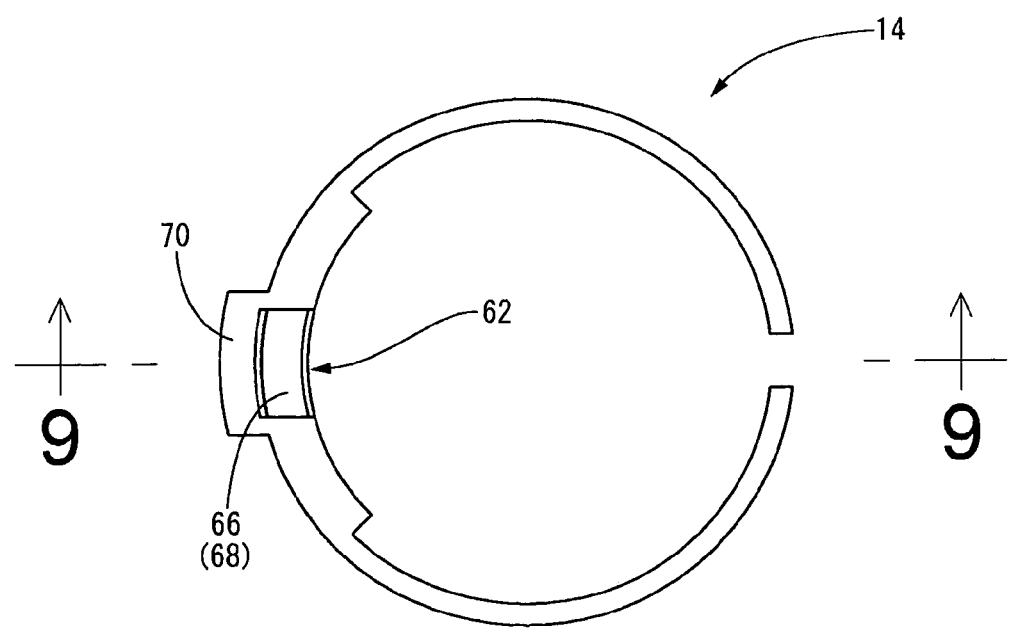
FIG. 10 is an illustration viewed in the direction of arrow 10 in FIG. 9.

As mentioned above, the split ring 14 is arranged to the inside of the lower end section of the housing 10 in which the reservoir unit 12 has been secured. This split ring 14 is composed, for example, of an elastically deformable molded resin article using resin material comparable to the material forming the housing 10. As shown in FIGS. 1, 9, and 10, the split ring 14 takes the form of a thin ring having outside diameter approximately equal to or slightly larger than the inside diameter of the housing 10, which has been divided by removing a segment of prescribed circumferential length at a single location along the circumference.

The section situated to the opposite side in the diametrical direction from this divided section of the split ring 14 is thicker in the diametrical direction, and an engaging hook 62 integrally projects up from the inside peripheral section of the end face of this thick portion. This engaging hook 62 has an extended portion 64 integrally extending upward from the end face of the split ring 14, and an engaging claw portion 66 integrally formed at the distal end of this extended portion 64. A sloping face 68 that slopes downwardly towards the outside in the diametrical direction of the split ring 14 is formed on the engaging claw portion 66. This sloping face 68 is designed so that its lower edge is situated at the same location with the outside peripheral face of the split ring 14 with respect to the diametrical direction of the split ring 14. An operating projection 70 of rectangular shape projects integrally out from the outside peripheral face of the split ring 14 in the zone thereof where the engaging hook 62 is formed.

As shown in FIG. 1, the split ring 14, oriented so that the engaging hook 62 extends upward and with its gap spread apart in the diametrical direction, is slipped externally about the small-diameter portion 48 of the reservoir ring 30 in the reservoir unit 12 which is situated to the inside of the lower end part of the housing 10. In this state, the split ring 14, having been placed in a state of constricted diameter through slight preliminary compression, is inserted into the housing 10 while positioning the operating projection 70 so as to project out through the window 24 which has been provided at the lower end of the housing 10. Through engagement of the operating projection 70 against the inside peripheral face of the window 24 inside the lower end part of the housing 10, the split ring 14 is fixedly positioned such that relative displacement in the circumferential and axial directions with respect to the housing 10 is not possible.

Figure 17:
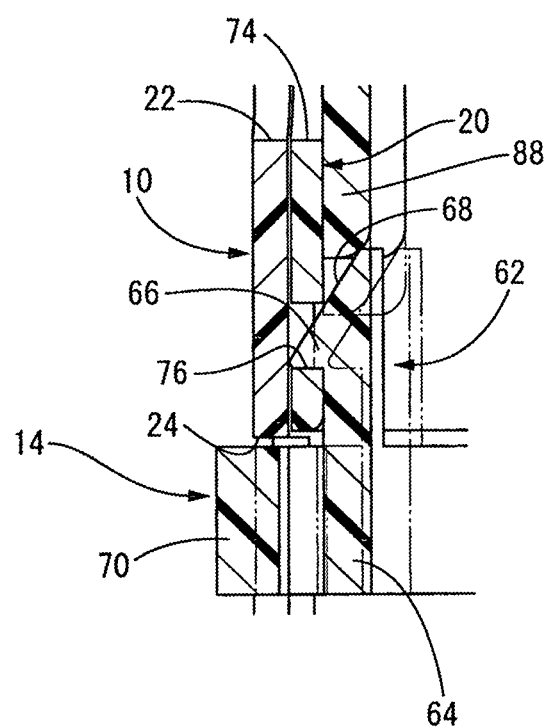
FIG. 17 is an enlarged fragmentary view of a part 17 in FIG. 16.

Thus, when the operating projection 70 is subjected to pushing operation from the outside, the outside peripheral face of the split ring 14 will slide along the inside peripheral face of the housing 10 and the split ring 14 will flex and constrict in diameter, whereby the engaging hook 62 will undergo displacement inwardly in the diametrical direction of the split ring 14 (see FIG. 17). If the sloping face 68 of the engaging hook 62 is subjected to downward pushing force, the split ring 14 will likewise flex and constrict in diameter, and the engaging hook 62 will undergo displacement inwardly in the diametrical direction of the split ring 14 (see FIG. 17).

Meanwhile, the push button 20 is inserted into the upper opening of the housing 10 as depicted in FIGS. 1 and 2. This push button 20 is a molded resin component made using resin material comparable to the material forming the housing 10. Its one-sided bottomed round cylindrical shape is provided with an upper base portion 72, and has outside diameter slightly smaller than the inside diameter of the housing 10 and length shorter than the housing 10. In two zones situated in opposition in the diametrical direction of the cylindrical wall of the push button 20 there are provided slits 74, 74 that extend for mutually identical length in the axial direction. These slits 74, 74 have width and length identical to the slits 22, 22 which have been provided to the housing 10. To the lower side (opening side) of one slit 74, an engaging hole 76 of slit form provided as an engaging portion extending in the circumferential direction passes completely through the cylindrical wall.

This push button 20 is then slipped inside the housing 10 through the upper opening of the housing 10, so that its upper base part lies exposed to the outside through the upper opening of the housing 10, and is positioned with the two slits 74, 74 of the push button 20 respectively aligned with the two slits 22, 22 of the housing 10. With the push button 20 in this state of being slipped inside the housing 10, it will be possible for it to slide in the vertical direction (axial direction) while sliding along the inside peripheral face of the housing 10, with slide in the downward direction being permitted up to the point that the lower end face comes into abutment against the upper end face of the split ring 14. When the push button 20 has been slid downward until reaching a bottom dead point location at which its lower end face is in abutment against the upper end face of the split ring 14, the engaging claw portion 66 of the engaging hook 62 of the split ring 14 will intrude into the engaging hole 76 of the push button 20 so as to become engaged therein (see FIG. 15). Through this engaged state the push button 20 will be prevented from sliding.

Figure 11:
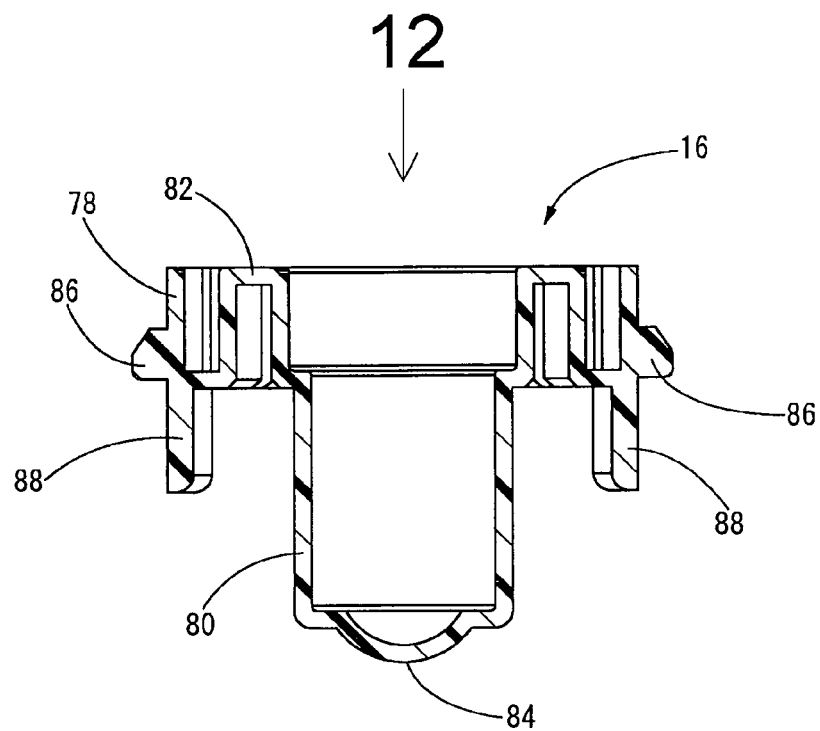
FIG. 11 is a longitudinal sectional view of a plunger which is part of the liquid medicine self-administration device of FIG. 1, taken along line 11-11 in FIG. 12.
Figure 12:
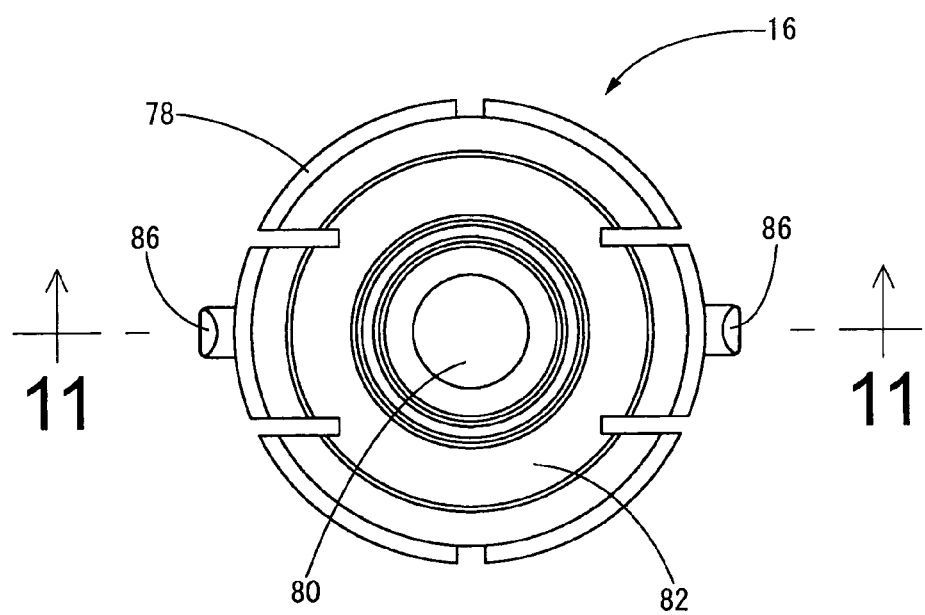
FIG. 12 is an illustration viewed in the direction of arrow 12 in FIG. 11.

The plunger 16 is housed between the push button 20 and the reservoir 28 in the axially medial part of the housing 10 interior. This plunger 16 is likewise made of appropriately selected material comparable to that of the housing 10. As shown in FIGS. 11 and 12, the plunger 16 integrally incorporates a slide ring portion 78 of ring shape as a whole having outside diameter slightly smaller than the inside diameter of the push button 20; a pushing cylinder portion 80 of one-sided bottomed round cylindrical shape having a lower base portion and positioned coaxially to the inside of the slide ring portion 78 and spaced apart therefrom by a prescribed distance in an attitude extending out towards the bottom from the lower opening of the slide ring portion 78; and a linking portion 82 linking the slide ring portion 78 with the pushing cylinder portion 80.

In this plunger 16, the lower face of the lower base part of the pushing cylinder portion 80 constitutes a pushing face 84 which is positioned in opposition in the axial direction to the upper base face of the reservoir 28. Slide projections 86, 86 are provided integrally projecting respectively at two locations situated at either side of the outside peripheral face of the slide ring portion 78 in the diametrical direction. Additionally, in each of the two zones of the slide ring portion 78 in which these two slide projections 86, 86 are respectively disposed there is integrally formed one disengaging projection 88, provided as disengaging means, which is defined by extending the section downward by a prescribed length. The inside angle part of the distal end part of the disengaging projection 88 is shaped as a convex curving angled part, giving it a rounded contour.

As depicted in FIG. 1, in the interior of the housing 10, the plunger 16 is positioned housed inside the lower opening of the push button 20. The two slide projections 86, 86 which have been provided to the slide ring portion 78 of the plunger 16 insert into and pass through the two slits 74, 74 of the push button 20, and respectively intrude into the slits 22, 22 of the housing 10. The plunger 16 is thereby rendered immovable in the circumferential direction within the housing 10, yet is capable of relative sliding in the axial direction (vertical direction) with respect to the push button 20 while guided by the slits 74, 22 which have been respectively provided in the push button 20 and the housing 10. When the push button 20 experiences relative movement towards the top of the housing 10, the two slide projections 86, 86 will become wedged between the upper ends of the slits 22, 22 of the housing 10 and the lower ends of the slits 74, 74 of the push button 20, thus preventing the push button 20 from being pulled out from inside the housing 10.

As will be understood from FIG. 1, the helical compression spring 18, which has shorter axial length than the push button 20, is accommodated positioned coaxially inside the push button 20 in which the plunger 16 has been housed. This helical compression spring 18 is attached at one end thereof to a mounting portion 90 that has been integrally formed on the inside face of the upper base portion 72 of the push button 20 (not shown), while the other end is secured to the linking portion 82 of the plunger 16.

Figure 13:
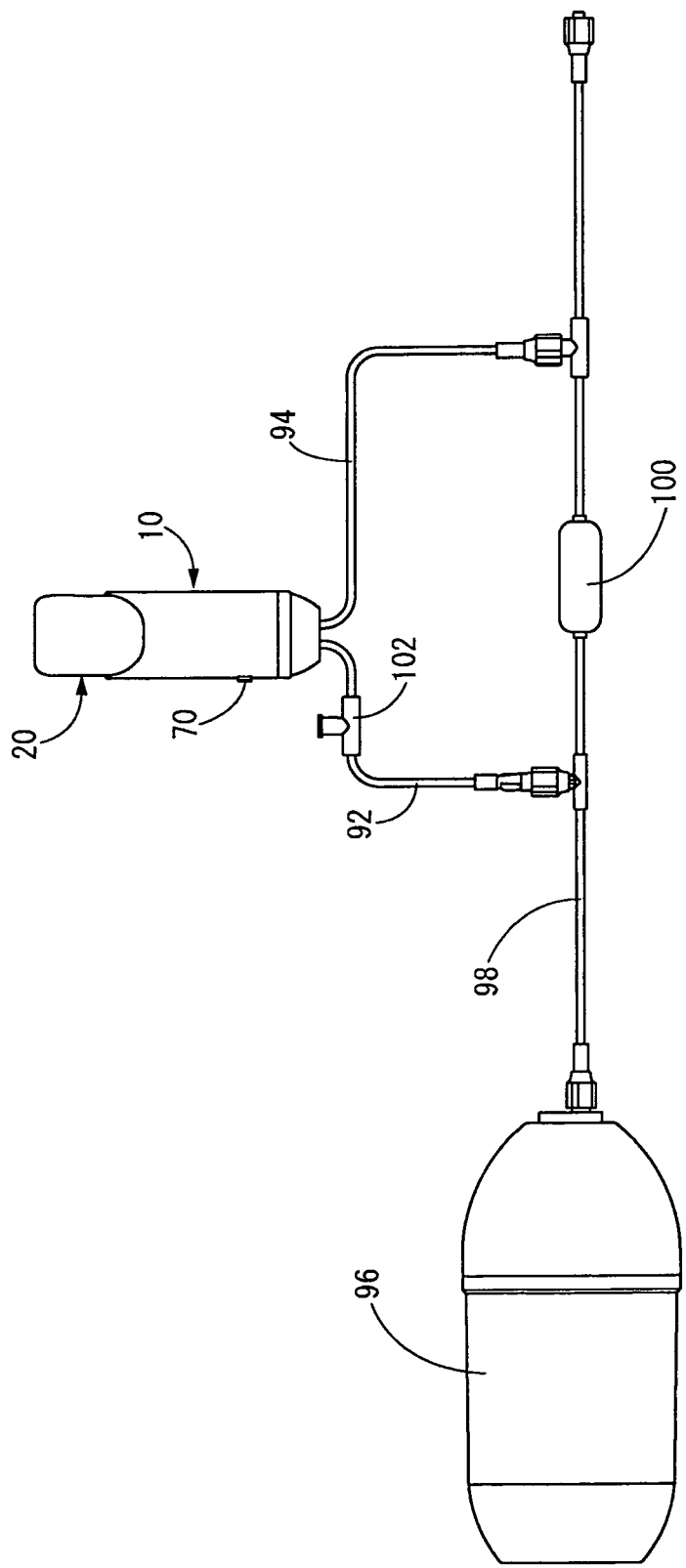
FIG. 13 is an illustration depicting a liquid medicine administration system that includes the liquid medicine self-administration device of FIG. 1 connected to a liquid medicine receptacle.

The plunger 16 is thereby attached to the upper base portion 72 of the push button 20 through the agency of the helical compression spring 18. When the plunger 16 and the upper base portion 72 of the push button 20 have come into proximity through relative movement of the push button 20 and the plunger 16 in their respective axial directions, the helical compression spring 18 becomes compressed, and the restoring force produced thereby urges the push button 20 and the plunger 16 in the direction of their separation.

Where the liquid medicine self-administration device of the present embodiment constructed as described above is to be placed in service, the liquid medicine inlet port 38 and the liquid medicine outlet port 40 of the base member 26 may be connected to a liquid medicine inlet tube 92 and a liquid medicine outlet tube 94 as depicted in FIG. 13, for example (the respective connection sections are not illustrated). The liquid medicine inlet tube 92, at the end thereof opposite that connected to the liquid medicine inlet port 38, is connected to the upstream end of a liquid medicine delivery tube 98 adapted to deliver to a catheter (not shown) or the like a prescribed liquid medicine such as an analgesic contained in a liquid medicine receptacle 96; while the liquid medicine outlet tube 94, at the end thereof opposite that connected to the liquid medicine outlet port 40, is connected to the downstream side. That is, in this instance, the liquid medicine self-administration device for providing an additional dose of liquid medicine is disposed in a parallel arrangement with the line composed of the liquid medicine delivery tube 98 for continuous administration of liquid medicine. Thus, continuous administration of liquid medicine may take place even while liquid medicine is retained in the liquid medicine retaining portion 60 of the liquid medicine self-administration device. In FIG. 13, 100 denotes a flow control device for controlling the flow rate of liquid medicine inside the liquid medicine delivery tube 98, and 102 denotes a port for connection of a syringe or the like.

The discussion now turns to the method of use of the liquid medicine self-administration device of the present embodiment.

First, with the liquid medicine self-administration device of the present embodiment connected in a parallel arrangement with the main line composed of the liquid medicine delivery tube 98 which leads from the liquid medicine receptacle 96 as depicted in FIG. 13, liquid medicine is continuously administered in a routine low dosage.

Figure 14:
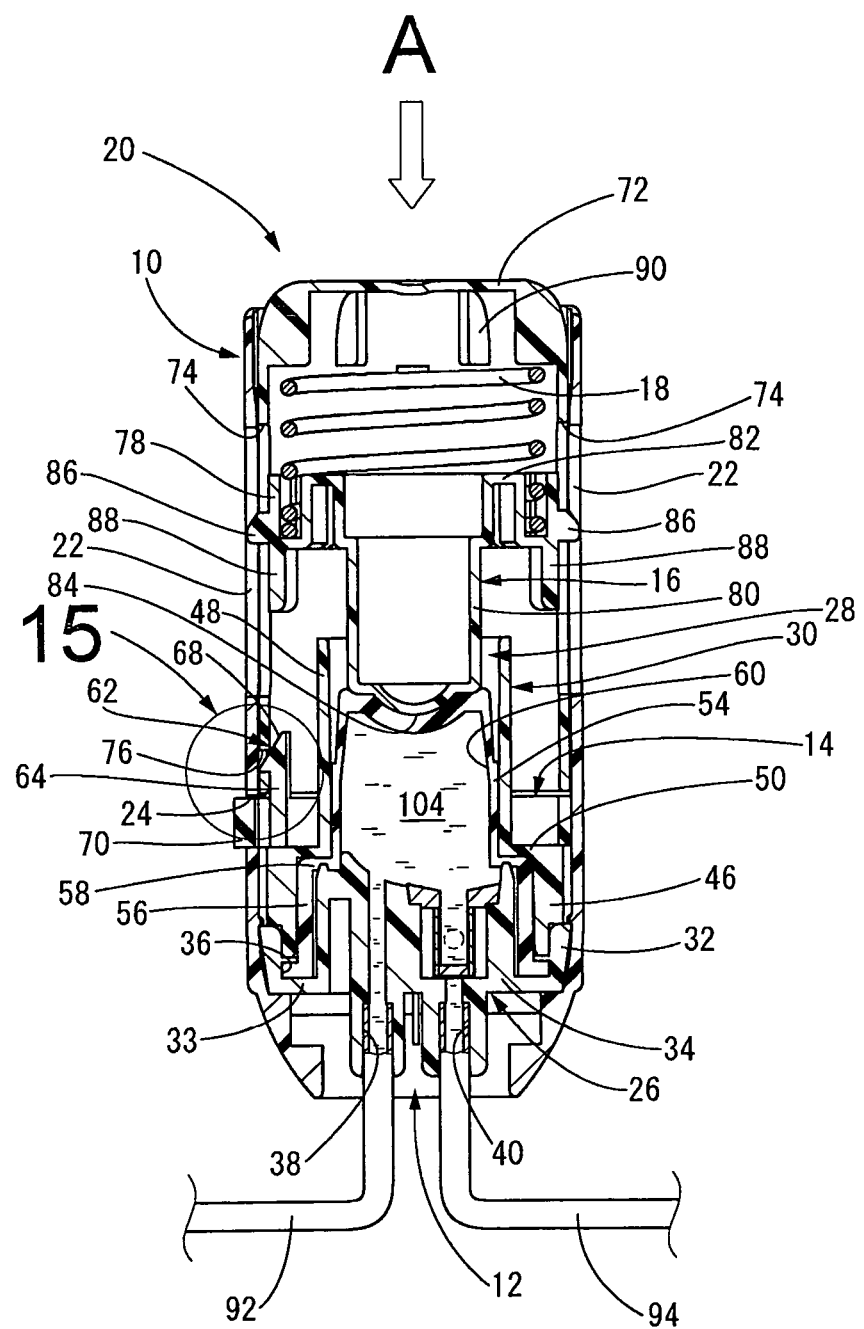
FIG. 14 is a drawing depicting a usage condition of the liquid medicine self-administration device of FIG. 1, and shows a condition immediately following pushing of a push button.
Figure 15:
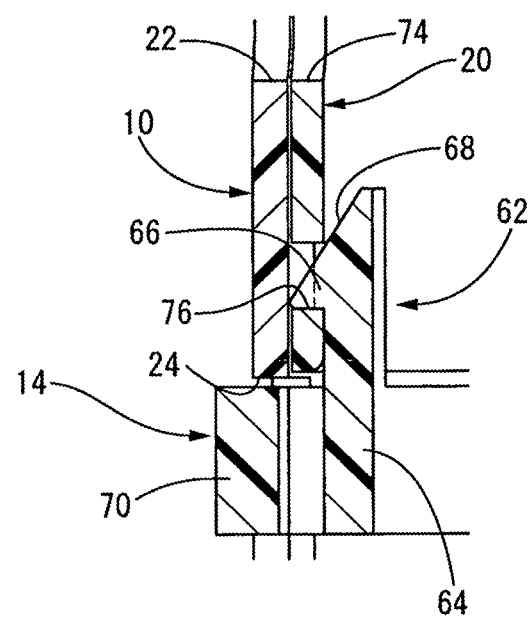
FIG. 15 is an enlarged fragmentary view of a part 15 in FIG. 14.

In the event that the patient needs to self-administer a one-time large dose of liquid medicine, the patient pushes the push button 20 downward (the direction indicated by arrow A) so that it slides downward while sliding along the inside peripheral face of the housing 10 as depicted in FIG. 14. At this time, because the two slide projections 86, 86 of the plunger 16 have been inserted through the slits 74, 74 of the push button 20, the push button 20 will slide straight ahead without axial rotation. Once the push button 20 has undergone sliding movement to the bottom dead point location at which its lower end face abuts against the upper end face of the split ring 14, the engaging claw portion 66 of the engaging hook 62 integrally formed with the split ring 14 will intrude into the engaging hole 76 provided at the lower end of the push button 20 and become engaged therein as depicted in FIGS. 14 and 15. Thus, the push button 20 will become locked in a state in which sliding movement is not possible, so that the push button 20 is held in place at the bottom dead point. From the above description it will be appreciated that in the present embodiment, the engaging means includes the engaging hole 76 of the push button 20, the engaging claw portion 66 of the engaging hook 62 of the split ring 14, and the sloping face 68 of the engaging claw portion 66.

Meanwhile, in association with downward sliding movement of the push button 20 the plunger 16, pushed by the helical compression spring 18, will move downward and the pushing face 84 will come into abutment against the upper base part of the reservoir 28. If the push button 20 experiences further downward sliding movement past this point, the helical compression spring 18 will become compressed between the upper base portion 72 of the push button 20 and the plunger 16.

Once the push button 20 is locked in the manner described above, starting at this point in time the helical compression spring 18 will begin to gradually expand due to restoring force. In association therewith, the plunger 16 will push against the small-diameter portion 54 of the reservoir 28 and will move downward while inducing small incremental flexural deformation thereof. Thus, liquid medicine 104 inside the liquid medicine retaining portion 60 of the reservoir 28 will be expelled out through the liquid medicine outlet port 40 and the liquid medicine outlet tube 94 connected thereto, and will pass through the liquid medicine delivery tube 98 to be delivered into the body of the patient through a catheter or the like. This expulsion of the liquid medicine 104 from the interior of the liquid medicine retaining portion 60 will proceed automatically on the basis of restoring force of the helical compression spring 18. At this time the liquid medicine 104 inside the liquid medicine retaining portion 60 will continue to be administered in a larger amount than during routine low-dose continuous administration, and will do so at a constant level of pressure. From the above description it will be appreciated that in the present embodiment, the pushing means includes the push button 20 and the plunger 16.

Figure 16:
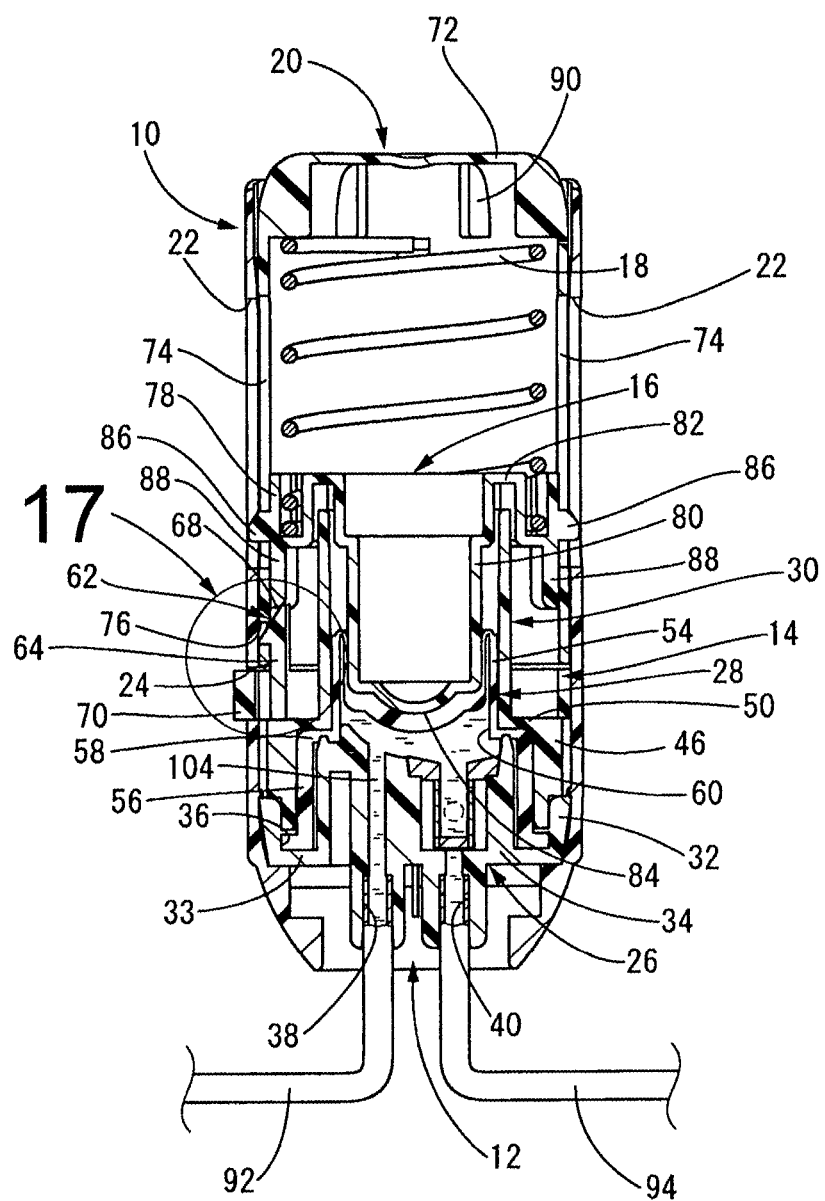
FIG. 16 is a drawing depicting another usage condition of the liquid medicine self-administration device of FIG. 1, and shows a condition in which, following pushing of the push button, the plunger has moved to the reservoir and induced pressure deformation of the reservoir.

Downward movement of the plunger 16 in association with such expansion of the helical compression spring 18 will cause the distal end part of the disengaging projection 88 which has been integrally formed with the plunger 16 to abut against the sloping face 68 of the engaging hook 62 as indicated by solid lines in FIGS. 16 and 17. As the plunger 16 moves further downward beyond this point, the disengaging projection 88 will move downward over the top of the sloping face 68 while pushing the sloping face 68 as indicated by double dot-and-dash lines in FIG. 17. The split ring 14 will thereby flex and constrict in diameter, and in association therewith the engaging hook 62 will experience displacement diametrically inward so that the engaging claw portion 66 disengages from the engaging hole 76 of the push button 20, releasing the push button 20 from its non-slidably locked condition. At this point, pushing force exerted on the plunger 16 due to restoring force of the helical compression spring 18, as well as pushing force on the reservoir 28 by the plunger 16, will both cease, thereby automatically terminating the expulsion of liquid medicine from inside the liquid medicine retaining portion 60 in a greater amount and at higher pressure than during routine low-dose continuous administration.

Subsequently, the small-diameter portion 54 of the reservoir 28 will recover to its condition prior to deformation through the pressure of injection of liquid medicine that is injected into the liquid medicine retaining portion 60 through the liquid medicine inlet port 38, and the liquid medicine retaining portion 60 interior will refill with liquid medicine 104. In association with this recovery of the small-diameter portion 54 of the reservoir 28, the plunger 16, the helical compression spring 18, and the push button 20 will be lifted upward and again return to their positions shown in FIG. 1. This completes preparation for a subsequent one-time administration of a large dose of liquid medicine by a pushing operation of the push button 20.

In the liquid medicine self-administration device of the present embodiment, one-time administration of a large dose of liquid medicine 104 can be automatically effected simply by pushing the push button 20 until the push button 20 locks. Subsequently, at the point in time that one-time administration of a large dose of liquid medicine 104 is completed, the push button 20 will unlock automatically even without performing any unlocking operation of the push button 20. Refilling of the liquid medicine retaining portion 60 of the reservoir 28 with liquid medicine 104 will then take place automatically as well.

Accordingly, where the liquid medicine self-administration device of the present embodiment is employed, it will be possible to effectively eliminate situations in which one-time administration of a large dose of liquid medicine through subsequent pushing operation of the push button 20 cannot be carried out due to having neglected to unlock the push button 20. A result of this is that further enhanced ease of use may be achieved a very advantageous manner.

Additionally, with this liquid medicine self-administration device, locking of the push button 20 (i.e. engagement of the engaging hook 62 by the engaging hole 76) can be released automatically simply through a process whereby the sloping face 68 of the engaging hook 62 is pushed by the disengaging projection 88 integrally formed with the plunger 16, owing to downward movement of the plunger 16 on the basis of restoring force of the helical compression spring 18. For this reason, the mechanism for unlocking the push button 20 can be realized advantageously through a very simple construction having a minimum of parts.

Furthermore, with the liquid medicine self-administration device of the present embodiment, the push button 20 may be unlocked manually through a push operation performed externally on the operating projection 70 to disengage the engaging hook 62 by the engaging hole 76. Thus, if for some reason it should become necessary to urgently unlock the push button 20, this can be accomplished quickly and reliably. Moreover, by unlocking the push button 20 manually during one-time administration of a large dose of the liquid medicine 104, automatic expulsion of a large dose of the liquid medicine 104 can be forcibly brought to an emergency halt.

Furthermore, with this liquid medicine self-administration device, through flexing and diameter constriction by the split ring 14, the engaging claw portion 66 is disengaged from the engaging hole 76 of the push button 20, unlocking the push button 20. Thus, as compared to a design wherein, for example, the engaging claw portion 66 is provided to a flexing member of plate or rod form, and the engaging claw portion 66 is disengaged from the engaging hole 76 of the push button 20 through flexural deformation of this plate-shaped flexing member, not only does the split ring 14 exhibit better durability to withstand repeated flexural deformation, but a larger deformation stroke can be assured as well. As a result, unlocking of the push button 20 can take place in a stable and reliable manner, and the robustness of the device as a whole can be advantageously improved.

While the present invention has been shown hereinabove in terms of certain specific arrangements, these are merely exemplary, and the invention is in no way limited by the disclosure herein.

Figure 18:
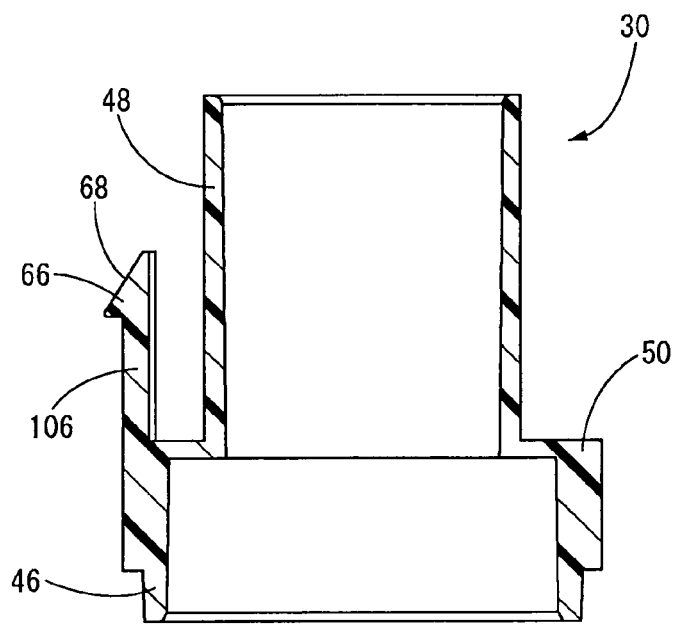
FIG. 18 is a drawing depicting another embodiment of the liquid medicine self-administration device according to the present invention and corresponds to FIG. 5.
Figure 19:
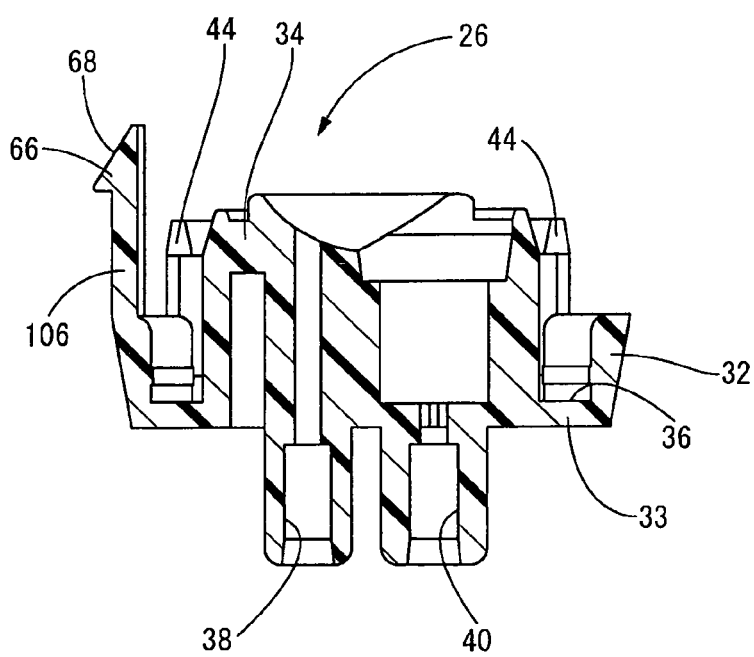
FIG. 19 is a drawing depicting yet another embodiment of the liquid medicine self-administration device according to the present invention and corresponds to FIG. 3.

For example, the construction of the flexing member to which the engaging claw portion 66 is provided is not limited in any way to that shown herein by way of example. As an example, as depicted in FIG. 18, a plate-shaped flexing piece 106 extending integrally upward could be provided to the step portion 50 of the reservoir ring 30, and the engaging claw portion 66 provided on the side face thereof. Alternatively, as depicted in FIG. 19, a plate-shaped flexing piece 106 extending integrally upward could be provided to the mounting ring portion 32 of the base member 26, and the engaging claw portion 66 provided on the side face thereof. Also, while not illustrated in the drawings, the plate-shaped flexing piece 106 integrally formed on the reservoir ring 30 or the base member 26 could be designed to undergo flexural deformation sideways, namely, in the axis-perpendicular direction, when the sloping face 68 provided to the engaging claw portion 66 is pushed by the disengaging projection 88 of the plunger 16. By so doing, the engaging claw portion 66 provided to the plate-shaped flexing piece 106 will separate from the engaging hole 76 of the housing 10 so that the engaging claw portion 66 disengages from the engaging hole 76.

It is possible in this way for the flexing member to be constituted as a flexing piece disposed at a fixed location so as to extend in the axial direction inside the housing 10. By so doing, the flexing member can be provided integrally with the other members, thereby advantageously affording a reduction in the number of parts. Moreover, with regard to the reservoir ring 30 depicted in FIG. 18 and the base member 26 depicted in FIG. 19, components and parts of similar construction to those in the reservoir ring 30 depicted in FIG. 5 and the base member 26 depicted in FIG. 3 have been assigned the same symbols used in FIGS. 5 and 3, and are not described in any detail.

In the preceding embodiment, the base member 26 was provided respectively with a liquid medicine inlet port 38 and a liquid medicine outlet port 40; however, as shown for example in FIG. 6 of U.S. Pat. No. 6,213,981, it would be possible to instead provide the base member 26 (termed a "port portion" in the publication in question) with a single inlet/outlet port for carrying out both intake and expulsion of liquid medicine.

Provided that the disengaging means is capable of movement in unison with the pushing member, it may be constituted as a separate member independent of the pushing member.

Further, whereas in the preceding embodiment the reservoir 28 is fabricated using elastic material, as long as this reservoir 28 has flexibility, it could be fabricated using non-elastic material instead. For example, it would be possible to use pliable resin material shaped into a bellows configuration.

It is also to be understood that the present invention may be embodied with various other changes, modifications and improvements, which may occur to those skilled in the art, without departing from the spirit and scope of the invention defined in the following claims, while detail illustrations for them are omitted.

What is claimed is:

1. A liquid medicine self-administration device comprising:
   a housing having a first open end and a second open end;
   a base member having a liquid medicine inlet/outlet port and attached to the housing, the base member fitting into the first open end of the housing;
   a flexible reservoir having an interior, an open end and a closed end, wherein the open end of the reservoir is closed by the base member, arranged accommodated within the housing with the interior in communication with the liquid medicine inlet/outlet port of the base member and adapted to retain liquid medicine that has been injected therein through the liquid medicine inlet/outlet port;
   an operating member inserted through the second open end of the housing and adapted to undergo movement into proximity with and away from the reservoir through an operation performed from an outside;
   engaging means adapted to engage the operating member when the operating member has moved into proximity with the reservoir and to prevent movement of the operating member;
   a constant pressure-opening valve fitted into an interior of a liquid medicine outlet port of the liquid medicine inlet/outlet port and adapted to open when pressure inside the liquid medicine outlet port has reached a predetermined value;
   a pushing member accommodated within the housing between the operating member and the reservoir so as to be capable of relative movement with respect to the operating member, and adapted, through relative movement with respect to the operating member, to push against and induce flexural deformation of the reservoir causing liquid medicine inside the reservoir to be expelled from the liquid medicine inlet/outlet port;
   a spring member that is accommodated positioned coaxially inside the operating member, and arranged within the housing in such a way as to undergo elastic deformation between the operating member and the pushing member through movement of the operating member into proximity with the reservoir, and to exhibit restoring force from an elastically deformed state in which the operating member has been engaged by the engaging means so that the relative movement of the pushing member with respect to the operating member resulting from the restoring force causes the reservoir to be pushed by the pushing member;

disengaging means arranged inside the housing so as to be capable of movement in unison with the pushing member and, when the pushing member has moved to a predetermined location while pushing the reservoir, functioning to release the engaging means from an engaged state with respect to the operating member; and a reservoir ring disposed externally about the reservoir while being diametrically inwardly spaced away from a side wall of the housing, and elongated in an axial direction such that the reservoir ring extends substantially the length of the reservoir; wherein after the engaging means is released from the engaged state with respect to the operating member by the disengaging means, the reservoir automatically refills with the liquid medicine, the reservoir ring has a stepped cylindrical shape, including a lower end section that defines a large-diameter portion, an upper end section that defines a small-diameter portion, and an axially medial section that defines a step portion, the reservoir has a bottomed stepped cylindrical shape that is smaller than the reservoir ring and has an upper base panel, and includes an upper section that defines a small-diameter portion, a lower section that defines a large-diameter portion, and an axially medial section that defines a step portion, and the reservoir ring is slipped externally about the reservoir such that the small-diameter portion of the reservoir ring corresponds with the small-diameter portion of the reservoir, the large-diameter portion of the reservoir ring corresponds with the large-diameter portion of the reservoir, and the step portion of the reservoir ring is juxtaposed over the step portion of the reservoir.

2. The liquid medicine self-administration device according to claim 1, wherein the disengaging means is composed of a disengaging projection integrally projecting towards the base member from the pushing member; wherein the engaging means includes an engaging portion disposed on the operating member, a flexing member capable of flexural deformation non-displaceably disposed between the reservoir and the pushing member, an engaging claw portion projecting from the flexing member and adapted to engage the engaging portion of the operating member, and a sloping face adapted to be pushed by the disengaging projection when the pushing member has moved towards the reservoir end and to bring about flexural deformation of the flexing member; and wherein the engaging claw portion is released from the engaged state with respect to the engaging portion of the operating member through flexural deformation of the flexing member in association with pushing of the sloping face by the disengaging projection.

3. The liquid medicine self-administration device according to claim 2, wherein the flexing member is composed of a split ring; and the engaging claw portion is released from the engaged state with respect to the engaging portion of the operating member through flexion and diameter constriction of the split ring brought about by the disengaging projection of the pushing member pushing against the sloping face, while the split ring is disposed externally about the reservoir ring.

4. The liquid medicine self-administration device according to claim 2, wherein the flexing member is composed of a flexing piece whose basal end is disposed at a fixed location inside the housing so as to extend in an axial direction; and the engaging claw portion is released from the engaged state with respect to the engaging portion of the operating member through flexural deformation of the flexing piece in an axis-perpendicular direction brought about by the disengaging projection of the pushing member pushing against the sloping face.

5. The liquid medicine self-administration device according to claim 2, wherein the engaging means is situated housed inside the housing having a window; and the flexing member is furnished with an operating projection that projects to an exterior of the housing through the window so that, with the engaging claw portion in the engaged state with respect to the engaging portion of the operating member, the flexing member undergoes flexural deformation when the operating projection is pushed from the outside, in order to release the engaging claw portion from the engaged state with respect to the engaging portion of the operating member.

6. The liquid medicine self-administration device according to claim 3, wherein the split ring has a divided section in one location along a circumference thereof, and has a thick section situated to an opposite side in a diametrical direction from the divided section, while the engaging claw portion and an operating projection that projects to an exterior of the housing through a window operable to release the engaging claw portion from the engaged state with respect to the engaging portion of the operating member, are integrally formed at the thick section.

7. The liquid medicine self-administration device according to claim 1, wherein the engaging means is disposed in a diametrical space between the housing and the reservoir ring.

* * * * *